(12) United States Patent
Jeong

(10) Patent No.: US 11,534,509 B2
(45) Date of Patent: Dec. 27, 2022

(54) SKIN CARE DEVICE

(71) Applicant: LG ELECTRONICS INC., Seoul (KR)

(72) Inventor: Hwoasu Jeong, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 548 days.

(21) Appl. No.: 16/617,673

(22) PCT Filed: Apr. 19, 2018

(86) PCT No.: PCT/KR2018/004541
§ 371 (c)(1),
(2) Date: Nov. 27, 2019

(87) PCT Pub. No.: WO2018/236036
PCT Pub. Date: Dec. 27, 2018

(65) Prior Publication Data
US 2020/0093945 A1 Mar. 26, 2020

(30) Foreign Application Priority Data
Jun. 19, 2017 (KR) ........................ 10-2017-0077143

(51) Int. Cl.
*A61L 2/10* (2006.01)
*A61H 23/02* (2006.01)
(Continued)

(52) U.S. Cl.
CPC .............. *A61L 2/10* (2013.01); *A61H 23/02* (2013.01); *A61L 2/24* (2013.01); *A61M 37/0092* (2013.01);
(Continued)

(58) Field of Classification Search
CPC .......... A61L 2/10; A61L 2/24; A61L 2202/14; A61L 2202/24; A61L 2/26; A61L 2/0047;
(Continued)

(56) References Cited

U.S. PATENT DOCUMENTS 7,981,112 B1 * 7/2011 Neev .................... A61B 18/203
607/98
2007/0038206 A1 2/2007 Altshuler et al.
(Continued)

FOREIGN PATENT DOCUMENTS

CN 201366065 Y 12/2009
CN 102348425 A 2/2012
(Continued)

*Primary Examiner* — David A Vanore
(74) *Attorney, Agent, or Firm* — Birch, Stewart, Kolasch & Birch, LLP

(57) ABSTRACT

Provided is a skin care device including a head part brought into contact with skin of a user, a battery configured to supply power for operation of the head part, a body part having a fastening portion provided at one end to which the head part is fastened and provided with the battery therein, and a cap assembly detachably attached to one end of the body part and forming an accommodation space configured to accommodate the head part, wherein the cap assembly includes a sterilization module disposed to irradiate ultraviolet light toward the head part when the cap assembly accommodates the head part.

14 Claims, 9 Drawing Sheets

(51) Int. Cl.
    *A61L 2/24*     (2006.01)
    *A61M 37/00*     (2006.01)
    *A61N 1/04*     (2006.01)
    *A61N 5/06*     (2006.01)
    *H04R 1/02*     (2006.01)

(52) U.S. Cl.
CPC .......... *A61N 1/0428* (2013.01); *A61N 5/0625* (2013.01); *H04R 1/028* (2013.01); *A61L 2202/11* (2013.01); *A61L 2202/14* (2013.01); *A61L 2202/24* (2013.01); *A61N 2005/0652* (2013.01)

(58) Field of Classification Search
CPC ............. A61M 37/0092; A61N 1/0428; A61N 5/0625; A61N 2005/0662; A61N 2005/0644; A61N 5/0616; A61N 2005/0661; A61N 2007/0034; A61N 7/00; A61H 23/0245; A61H 2201/0153; A61H 2201/0207; A61H 2201/1207; A61H 2201/5007
See application file for complete search history.

(56) References Cited

U.S. PATENT DOCUMENTS

| | | | |
|---|---|---|---|
| 2013/0184693 A1* | 7/2013 | Neev | A61N 5/0617 606/9 |
| 2014/0135798 A1 | 5/2014 | David | |
| 2015/0100002 A1 | 4/2015 | Choi | |
| 2015/0313354 A1* | 11/2015 | Mongan | A61L 2/24 15/105 |
| 2016/0292365 A1* | 10/2016 | Chi | G16H 40/63 |
| 2019/0060660 A1* | 2/2019 | Lee | A61L 2/10 |
| 2020/0046999 A1* | 2/2020 | Lim | A61F 7/007 |
| 2020/0085015 A1* | 3/2020 | Yoo | A01K 13/002 |
| 2020/0087031 A1* | 3/2020 | Yoo | A01K 13/00 |
| 2020/0093945 A1* | 3/2020 | Jeong | H04R 1/028 |
| 2021/0153638 A1* | 5/2021 | Jeong | A46B 13/02 |
| 2021/0310637 A1* | 10/2021 | Yee | F21V 21/26 |
| 2021/0345767 A1* | 11/2021 | Zheng | A61L 2/10 |
| 2022/0031877 A1* | 2/2022 | Liao | B08B 3/12 |

FOREIGN PATENT DOCUMENTS

| | | |
|---|---|---|
| CN | 104918593 A | 9/2015 |
| CN | 105377362 A | 3/2016 |
| JP | 2017-70483 A | 4/2017 |
| KR | 10-2004-0092205 A | 11/2004 |
| KR | 10-0497139 B1 | 6/2005 |
| KR | 10-2014-0079602 A | 6/2014 |
| KR | 10-2015-0137441 A | 12/2015 |
| KR | 10-1649522 B1 | 8/2016 |
| KR | 10-2017-0017582 A | 2/2017 |
| KR | 10-2017-0030413 A | 3/2017 |

* cited by examiner

SKIN CARE DEVICE

CROSS REFERENCE TO RELATED APPLICATIONS

This application is the National Phase of PCT International Application No. PCT/KR2018/004541, filed on Apr. 19, 2018, which claims priority under 35 U.S.C. 119(a) to Patent Application No. 10-2017-0077143, filed in the Republic of Korea on Jun. 19, 2017, all of which are hereby expressly incorporated by reference into the present application.

BACKGROUND

The present disclosure relates to a skin care device, and more particularly, to a skin care device capable of accelerating skin absorption of a cosmetic product or massage the skin.

Skin care is aimed at maintaining blemish-free, clean and smooth skin, and most attention is directed to skin care of a face among body parts. Therefore, people wants to keep the skin clean by getting a massage, applying a functional cosmetic product, or using various cleaning products to care for facial skin.

Skin may act as a protective layer preventing penetration of various biological and chemical substances and loss of moisture from the interior. However, the function of the skin as a protective layer also makes it difficult to absorb beneficial active ingredients contained in cosmetic products or skin drugs.

Therefore, research into various physical and chemical methods for achieving effective absorption of the active ingredients by overcoming the function of the skin as a protective layer has been conducted. The physical methods include a method of letting the stratum corneum of skin to be transmitted by forming a temporary weak spot on the stratum corneum such as iontophoresis, electroporation, phonophoresis, microneedle, and the like.

Here, the method of using ultrasound such as ultrasonography or phonophoresis are known in various documents. Ultrasound of a high frequency mainly acts on a surface of skin, thereby providing more effective penetration of the active ingredient to the skin epidermis.

SUMMARY

An aspect of the present disclosure provides a skin care device capable of effectively caring skin by providing a combination of iontophoresis, ultrasound, a thermal function, high frequency, low frequency stimulation, and the like.

Another aspect of the present disclosure provides a skin care device having a cap assembly capable of performing a sterilization operation on a contact probe of a head part of a main body, while opening and closing the head part.

To achieve these and other advantages and in accordance with the purpose of the invention, as embodied and broadly described herein, there is provided a skin care device including: a head part brought into contact with skin of a user; a battery configured to supply power for operation of the head part; a body part having a fastening portion provided at one end to which the head part is fastened and provided with the battery therein; and a cap assembly detachably attached to one end of the body part and forming an accommodation space configured to accommodate the head part, wherein the cap assembly includes a sterilization module disposed to irradiate ultraviolet light toward the head part when the cap assembly accommodates the head part.

According to an embodiment, the head part may include a magnetic material, and the cap assembly may include a hall sensor configured to detect a change in a magnetic field due to the magnetic material when the head part is accommodated.

The sterilization module may include an ultraviolet light emitting device configured to irradiate the ultraviolet light toward the head part on the basis of the change in the magnetic field detected by the hall sensor.

According to an embodiment, the sterilization module may include a UV-C LED configured to irradiate ultraviolet light having a UV-C wavelength.

The cap assembly may include an outer body forming an appearance of the cap assembly and forming the accommodation space of the head part therein; and an inner body accommodated in the outer body, the sterilization module may be disposed between the outer body and the inner body, and the inner body may have an opening exposing the ultraviolet light emitting device included in the sterilization module to the accommodation space.

The cap assembly may further include a top cover mounted at one end of the outer body, and a battery accommodation space configured to accommodate a battery may be provided between the top cover and the outer body.

According to an embodiment, the skin care device may further include a head part sealing member formed between the head part and the fastening portion.

The head part may include: a contact probe brought into contact with the skin of the user and configured to allow a positive electrode or a negative electrode to be formed on a surface thereof according to an operation mode of the skin care device; an ultrasonic resonator configured to transmit ultrasonic vibration into the skin of the user; and a vibration motor configured to vibrate the contact probe and transfer vibration to the skin.

According to an embodiment, the contact probe may be fastened to the fastening portion to form a space configured to accommodate the ultrasonic resonator and the vibration motor therein, and a circumference of the surface of the contact probe may be smaller than a circumference of the fastening portion.

The body part may include a case forming an appearance of the body part; a board provided in the case; and a speaker module disposed between the case and the board.

The speaker module may include a speaker configured to output sound based on an operation state of the skin care device; a speaker seating portion fixed to the board and allowing the speaker to be seated thereon; and a speaker holder fastened to the speaker seating portion and configured to fix the speaker, wherein an echo space may be provided between the speaker and the speaker seating portion.

According to an embodiment, the speaker module may further include a sealing portion provided between the speaker and the speaker holder to shield the echo space from the outside.

The skin care device may further include a cradle mounted at the other end of the body part and configured to supply power for charging the battery.

The cradle may include a case forming an appearance of the cradle and forming an accommodation space configured to accommodate a portion of the other end of the body part; and a charging module provided in the case and including a power supply terminal connected to an external power supply, wherein a width of a lower portion of the case is larger than a width of an upper portion of the case.

The body part may include a body part magnetic material disposed to be adjacent to the other end in the case, and the cradle may include a cradle magnetic material having a polarity different from a polarity of the body part magnetic material.

It is to be understood that both the foregoing general description and the following detailed description of the present disclosure are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiments of the invention and together with the description serve to explain the principle of the invention. In the drawings.

DETAILED DESCRIPTION OF THE EMBODIMENTS

Hereinafter, the embodiments of the present invention will be described with reference to the accompanying drawings, in which like numbers refer to like elements throughout although the embodiments are different, and a description of the like elements a first embodiment will be used for those of the different embodiment. In the following description, usage of suffixes such as 'module', 'part' or 'unit' used for referring to elements is given merely to facilitate explanation of the present invention, without having any significant meaning by itself. In describing the present invention, if a detailed explanation for a related known function or construction is considered to unnecessarily divert the gist of the present invention, such explanation has been omitted but would be understood by those skilled in the art. The accompanying drawings of the present invention aim to facilitate understanding of the present invention and should not be construed as limited to the accompanying drawings. Also, the present invention is not limited to a specific disclosed form, but includes all modifications, equivalents, and substitutions without departing from the scope and spirit of the present invention.

It will be understood that, although the terms first, second, etc. may be used herein to describe various elements, these elements should not be limited by these terms. These terms are only used to distinguish one element from another.

It is to be understood that when one element is referred to as being "connected to" or "coupled to" another element, it may be connected directly to or coupled directly to another element or be connected to or coupled to another element, having the other element intervening therebetween. Meanwhile, it is to be understood that when one element is referred to as being "connected directly to" or "coupled directly to" another element, it may be connected to or coupled to another element without the other element intervening therebetween.

As used herein, the singular forms "a", "an" and "the" are intended to include the plural forms as well, unless the context clearly indicates otherwise.

It will be further understood that the terms "comprises" "comprising," "includes" and/or "including" when used herein, specify the presence of stated features, integers, steps, operations, elements, and/or components, but do not preclude the presence or addition of one or more other features, steps, operations, elements, components, and/or groups thereof.

Hereinafter, embodiments of the present disclosure will be described in detail with reference to the accompanying drawings.

Figure 1:
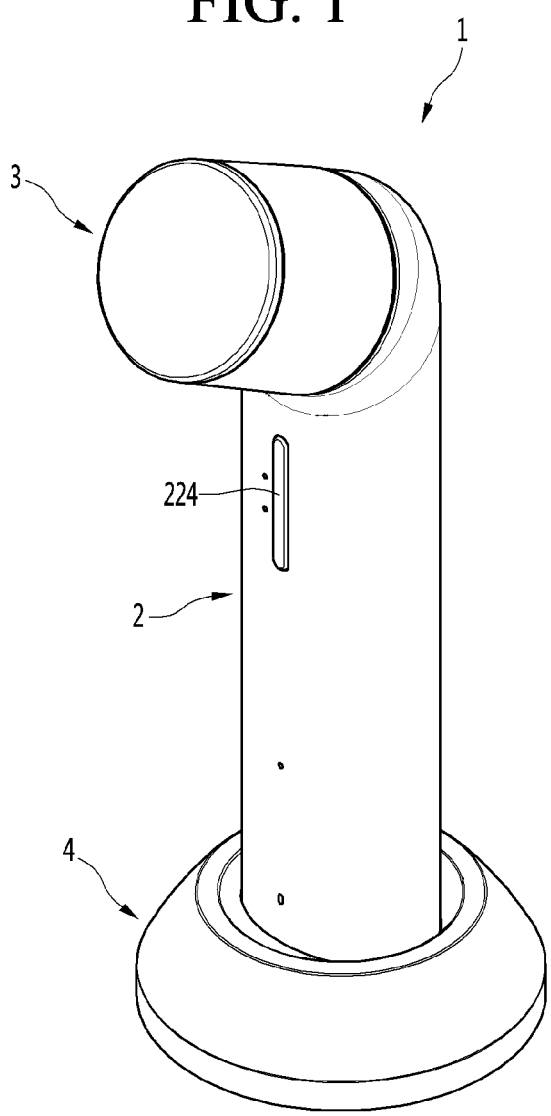
FIG. 1 is a perspective view of a skin care device according to an embodiment of the present disclosure.
Figure 2:
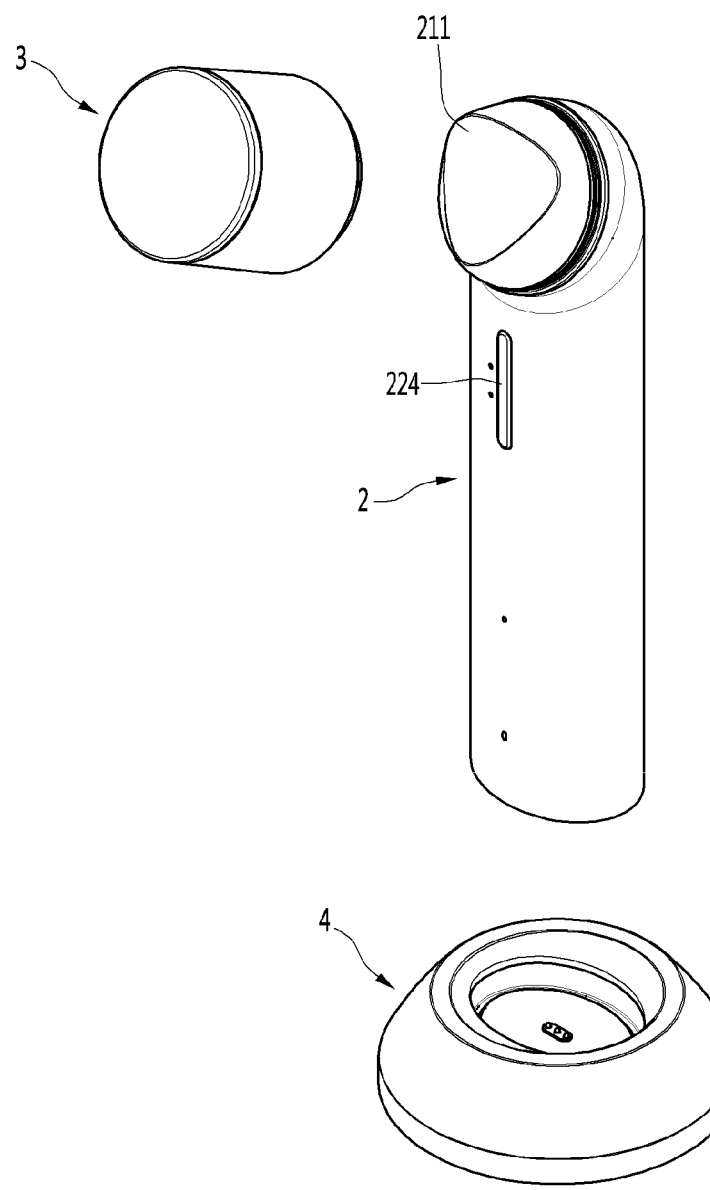
FIG. 2 is a perspective view illustrating a main body, a cap assembly, and a cradle included in a skin care device according to an embodiment of the present disclosure which are separated.

FIG. 1 is a perspective view of a skin care device according to an embodiment of the present disclosure, FIG. 2 is a perspective view when a main body, a cap assembly, and a cradle included in the skin care device according to an embodiment of the present disclosure are separated.

Referring to FIGS. 1 and 2, a skin care device 1 according to an embodiment of the present disclosure may be a device which applies a certain stimulation to skin of a user to remove a waste of the skin or to accelerate absorption of active ingredients applied to the skin. The skin care device 1 may include a main body 2, a cap assembly 3, and a cradle 4.

The main body 2 may have a shape allowing the user to easily grip the main body and bring one end having a contact probe 211 into close contact with skin to stimulate the skin. For example, a case 223 forming an appearance of the main body 2 may have at least a portion having a cylindrical shape, so that the user may easily grip the case 223 by hand.

The main body 2 may have the contact probe 211 at one end thereof. As illustrated in FIG. 2, one surface of the main body 2 on which the contact probe 211 is disposed may be inclined to form a certain angle with a bottom surface of the main body 2 but is not necessarily limited thereto.

According to an embodiment, an inclination angle of the contact probe 211 with respect to the case 223 may be freely adjusted within a predetermined angle range. In this case, as the inclination angle of the contact probe 211 is adjusted according to skin parts, thereby enabling more effective stimulation of a skin part in contact with the contact probe 211.

The main body 2 may include a button portion 224 for power on/off of the main body 2, switching of an operation mode, and the like. The operation mode may include a waste removal mode and an absorption acceleration mode but are not necessarily limited thereto.

The components included in the main body 2 and embodiments related to the operation mode will be described in more detail later with reference to FIG. 3.

The cap assembly 3 may be detachably attached to the main body 2 to open or close the contact probe 211 with respect to the outside. To this end, the cap assembly 3 may form an accommodation space for accommodating the contact probe 211 therein. For example, the cap assembly 3 may have a cylindrical shape with one side open.

In addition, the cap assembly 3 according to an embodiment of the present disclosure may have a sterilization module for sterilization of the contact probe 211 provided at the main body 2.

A configuration of the cap assembly 3 will be described later in more detail with reference to FIG. 4.

The cradle 4 may be connected to (or mounted at) the main body 2 to supply power for charging a battery provided at the main body 2. To this end, the cradle 4 may include a cradle contact terminal in contact with a main body contact terminal provided at the main body 2. For example, the main body 2 may have the main body contact terminal at a lower portion thereof, and in this case, the lower portion of the main body 2 may be inserted into the cradle 4 so that the main body 2 may be mounted on the cradle 4.

The cradle 4 has a cylindrical shape having a width increasing downward, thereby stably supporting the main body 2 when the main body 2 is mounted. In addition, an upper inner circumference of the cradle 4 may be equal to or larger than a lower outer circumference of the main body 2. Accordingly, when the main body 2 is mounted on the cradle 4, the cradle 4 may accommodate the lower portion of the main body 2 to thereby support the main body 2.

Figure 3:
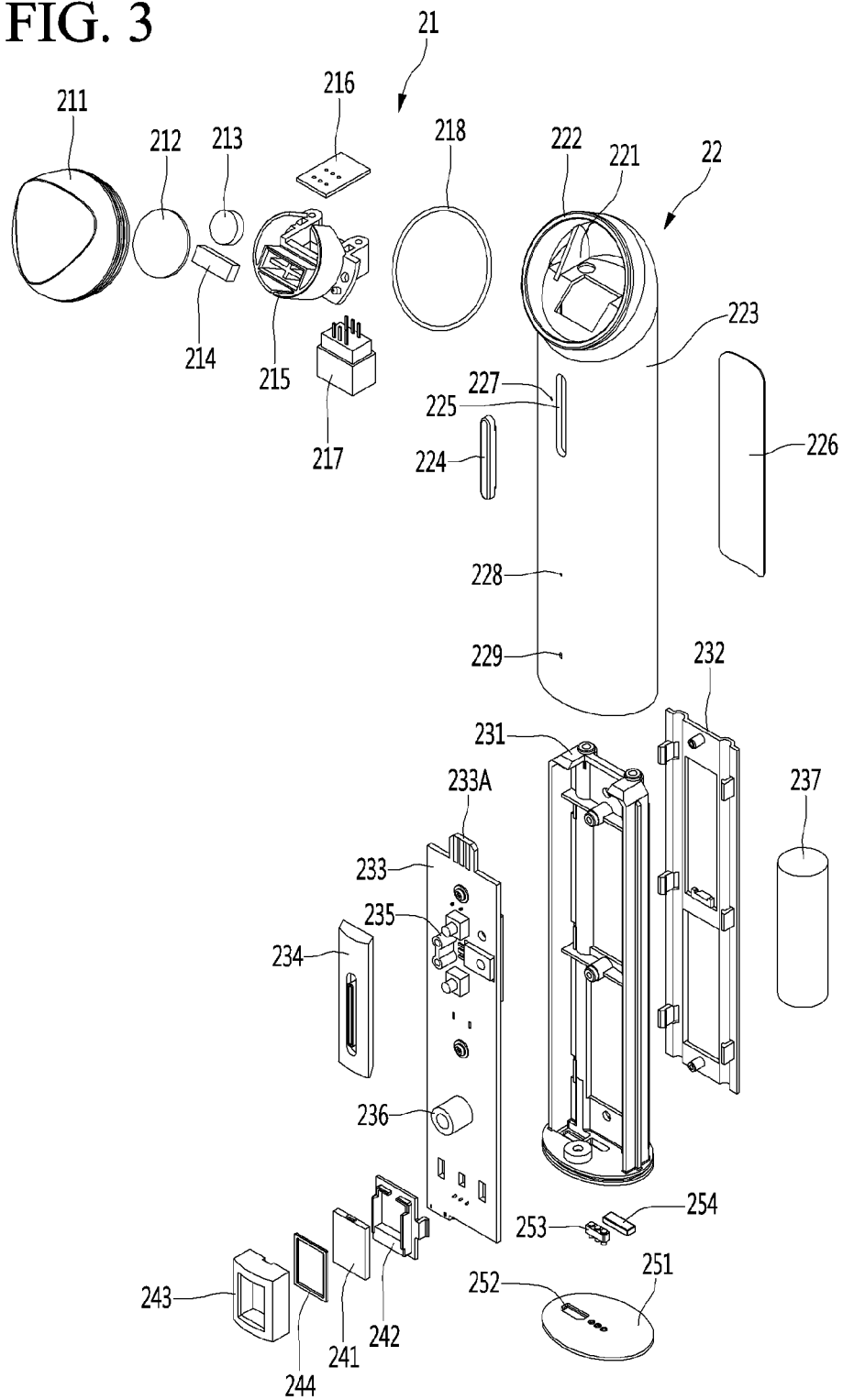
FIG. 3 is an exploded perspective view of a main body included in a skin care device according to an embodiment of the present disclosure.

FIG. 3 is an exploded perspective view of a main body included in a skin care device according to an embodiment of the present disclosure.

In the following drawings, the portion where the contact probe 211 of the main body 2 is disposed is defined as the upper portion, and the portion where the main body contact terminal 253 is disposed is defined as the lower portion.

Referring to FIG. 3, the main body 2 may include a head part 21 and a body part 22.

The head part 21 may include various components for removing wastes from the skin or accelerating absorption of active ingredients applied to the skin by applying stimulation to the skin part of the user in various ways.

The head part 21 may include the contact probe 211, an ultrasonic resonator 212, a vibration motor 213, a holder 215, a head part control module 216, a head part socket 217, and a head sealing portion.

The contact probe 211 may be brought into direct contact with the skin of the user and transmit stimulation to the skin of the user. The contact probe 211 may be formed to have a circumference or area reduced toward the contact portion surface from the fastening portion with the body part 22 in order to effectively contact a local part of the skin of the user. As the contact probe 211 is fastened to a contact probe fastening portion 222 of the body part 22, the other components included in the head part 21 may be accommodated in a space between the contact probe 211 and the body part 22.

A positive electrode or negative electrode may be formed on a surface of the contact probe 211 depending on an operation mode. In order to form ions at the contact probe 211, the contact probe 211 may be formed of a metal material. In addition, the surface of the contact probe 211 may be plated with platinum, gold, or the like in order to prevent occurrence of allergy of the skin when in contact with the skin of the user.

For example, when the skin care device 1 operates in a waste removal mode, positive electrodes may be formed on a surface of the contact probe 211. Meanwhile, when the skin care device 1 operates in an absorption acceleration mode, negative electrodes may be formed on the surface of the contact probe 211.

The ultrasonic resonator 212 may vibrate at a predetermined frequency to generate ultrasonic waves. For example, the ultrasonic resonator 212 may vibrate at a frequency of about 5 MHz to generate ultrasonic waves, and the ultrasonic waves generated by the ultrasonic resonator 212 may be delivered into the skin to accelerate absorption of active ingredients applied to the skin.

The vibration motor 213 may vibrate the contact probe 211 to transmit vibration to the skin in contact with the contact probe 211. As vibration is transmitted to the skin, a gap may occur in the stratum corneum of the skin, and a waste may be discharged to the outside through the gap of the stratum corneum or an active ingredient may be introduced into the skin.

Various components provided in the head part 21 may be mounted on or connected to the holder 215, and the holder may fix the various components to the main body 2. For example, the holder 215 may be provided with a mounting space or an accommodation space in which the vibration motor 213, the head part control module 216, the head part socket 217, and the like are mounted or accommodated.

The holder 215 may be fastened to the holder fastening portion 221 of the body part 22 (to be described later) so as to be fixed to the body part 22.

The head part control module 216 may control an operation of the components included in the head part 21. Specifically, the head part control module 216 may control the operation of the ultrasonic resonator 212 or the vibration motor 213. The head part control module 216 may include a controller such as an integrated circuit or a microcomputer, and the controller may control the operation of the components included in the head part 21.

The head part socket 217 may transfer power supplied from a battery 237 included in the body part 22 to the components of the head part 21. The head part socket 217 may be mounted at the holder 215.

The head sealing portion 218 may prevent water, cosmetics, and the like from penetrating between the head part 21 and the body part 22. The head sealing portion 218 may have a ring shape and may be provided between the contact probe 211 and the contact probe fastening portion 222. For example, the head sealing portion 218 may be formed of a material such as rubber or silicon.

According to an embodiment, the head part 21 may further include a magnetic material 214 for detecting whether the head part 21 or the contact probe 211 is accommodated in the cap assembly 3. When the contact probe 211 is accommodated in the accommodation space of the cap assembly 3 as the cap assembly 3 is mounted at the head part 21 of the main body 2, a hall sensor provided in the cap assembly 3 (not shown) may detect that the contact probe 211 is accommodated by detecting a change in a magnetic field due to proximity of the magnetic material 214.

According to an embodiment, the head part 21 may further include a thermal portion (not shown) for increasing a temperature of the contact probe 211. The thermal portion may be implemented as a thermal LED, coil, or the like.

When the contact probe 211 whose temperature is increased due to the thermal portion comes into contact with a skin surface, pores present on the skin surface may be expanded. As the pores are expanded, waste products in the skin may be more effectively discharged or active ingredients on the skin surface may be smoothly absorbed into the skin. When the thermal portion is included in the head part 21, the head part 21 may further include a temperature sensor (not shown) detecting a temperature of the contact probe 211 to prevent the contact probe 211 from being overheated by the thermal portion to cause a burn on the skin. If the temperature detected by the temperature sensor exceeds a predetermined temperature, the operation of the thermal portion may be stopped.

Referring to FIG. 3, the body part 22 may include a holder fastening portion 221, a contact probe fastening portion 222, a case 223, a button portion 224, and an electrode plate 226. In addition, an inner frame 231, an inner frame cover 232, a board 233 including a main control module, an operation mode LED 235, a battery LED 236, a battery, speaker modules 241, 242, 243, and 244, a lower cover 251, and a main body contact terminal 253 may be provided inside and at a lower portion of the body part 22.

The holder fastening portion 221 may be fastened to the holder 215 through a screw or the like. The holder 215 may be fixed to the body part 22 according to the holder fastening portion 221.

As the contact probe fastening portion 222 is fastened to the contact probe 211, the contact probe 211 may be fixed to the body part 22. As described above, a space for accommodating various components of the head part 21 may be provided between the contact probe 211 and the body part 22.

For example, the contact probe fastening portion 222 may form a spiral guide protrusion to which the contact probe 211 is to be inserted and fastened, while being rotated. In this case, a spiral groove may be formed at the contact probe 211. Conversely, a spiral groove may be formed at the contact probe fastening portion 222 and a guide protrusion may be formed at the contact probe 211.

The case 223 may form an outer appearance of the main body 2 and form an accommodation space that accommodates various configurations for the operation of the main body 2 therein. As described above with reference to FIGS. 1 and 2, at least a portion of the case 223 may have a cylindrical shape so that the user may easily grip it by hand.

The case 223 may be provided with a main body portion through-groove 225 for the button portion 224 connected to the internal board 233 or the button fixing portion 234 to protrude to the outside.

In addition, the case 223 may further include light irradiation holes 227 and 228 for light emitted from each of the operation mode LED 235 and the battery LED 236 connected to the internal board 233 to be irradiated to the outside.

The button portion 224 may include a power button for turning on/off power of the main body 2 and an operation mode button for changing an operation mode of the main body 2. As shown in FIG. 3, the power button and the operation mode button of the button portion 224 may be integrally formed. In this case, one side of the button portion 224 may correspond to the power button and the other side thereof may correspond to the operation mode button. According to an embodiment, the button portion 224 may include a power button and an operation mode button separated from each other.

The electrode plate 226 may be electrically connected to the contact probe 211 and may have a polarity different from that of the contact probe 211. Specifically, the contact probe 211 may be electrically connected to one of positive and negative electrodes of the battery 237, and the electrode plate 226 may be electrically connected to the other electrode of the battery 237. According to an operation mode of the main body 2, electrodes to which the contact probe 211 and the electrode plate 226 are respectively connected may vary.

The electrode plate 226 may be provided to be exposed to one surface of the case 223, so that the electrode plate 226 may come into contact with the user's hand when the user grips the case 223. As the electrode plate 226 comes into contact with the user's hand and the contact probe 211 comes into contact with the skin of the user, a closed circuit connecting the battery 237, the contact probe 211, the user's main body, the electrode plate 226, and the battery 237 may be configured.

Accordingly, current flows from the battery 237 to the user's main body, thereby removing wastes from the skin or accelerating absorption of active ingredients.

Various components inside the main body 2 may be mounted on or connected to the inner frame 231. For example, the holder fastening portion 221, the board 233, the battery 237, the lower cover 251, or the like may be connected or mounted on the inner frame 231.

The board 233 may be provided with a controller for controlling an overall operation of the main body 2. The controller may be implemented as an integrated circuit (IC), a microcomputer, an embedded processor, a controller, an application processor (AP), or the like. The controller may control a polarity of ions formed at the contact probe 211, an operation of the ultrasonic resonator 212, an operation of the vibration motor 213, and the like according to an operation mode of the main body 2.

In detail, when power of the main body 2 is turned on and an operation mode of the main body 2 is selected, the controller included in the board 233 may directly control the operation of the components included in the head part 21 according to the selected operation mode or indirectly control the operation of the components by transmitting a control signal in accordance with the operation mode to the head part control module 216.

Hereinafter, it is assumed that the controller directly controls the operation of the components included in the head part 21.

For example, when the operation mode is selected as the waste removal mode, the controller may control to form a positive electrode on the surface of the contact probe 211. In this case, the contact probe 211 may be electrically connected to a positive electrode of the battery 237 and the electrode plate 226 may be electrically connected to a negative electrode of the battery 237. As the positive electrode is formed on the surface of the contact probe 211, wastes having a negative polarity present in the stratum corneum of the skin may be pulled by an attractive force with the contact probe 211 so as to be discharged to the outside of the skin.

In addition, the controller may drive the vibration motor 213 to vibrate the skin, thereby smoothly discharging the wastes. According to an embodiment, when the head part 21 is provided with a thermal portion (e.g., a thermal LED or a coil, etc.), the controller may extend the pores of the skin by driving the thermal portion to allow the wastes to be discharged more smoothly.

Meanwhile, when the operation mode is selected as absorption acceleration mode, the controller may control to form a negative electrode on the surface of the contact probe 211. In this case, the contact probe 211 may be electrically connected to the negative electrode of the battery 237 and the electrode plate 226 may be electrically connected to the positive electrode of the battery 237. As the negative electrode is formed on the surface of the contact probe 211, the active ingredients having a negative (−) polarity present on the surface of the skin may be pushed out by a repulsive force with the contact probe 211 so as to be injected and absorbed into the skin.

In addition, the controller may drive the ultrasonic resonator 212 and the vibration motor 213 to vibrate the stratum corneum of the skin, thereby accelerating absorption of the active ingredients. According to an embodiment, when the head part 21 has a thermal portion, the controller may extend the pores of the skin by driving the thermal portion so that the active ingredients may be more smoothly absorbed.

According to an embodiment, the board 233 may further include a communication unit for communication with a terminal such as a smartphone or a tablet PC. The controller may transmit information on a sterilization operation of the cap assembly 3, battery information of the main body 2, and the like to the terminal through the communication unit.

The board 233 may include the button portion 224 for turning on/off power of the main body 2 or changing the operation mode of the main body 2, at least one operation mode LED 235 indicating information on the currently selected operation mode, and a battery LED 236 indicating a battery status.

The operation mode LED 235 may inform the user of information on the currently selected operation mode. To this end, the operation mode LED 235 may include a plurality of operation mode LEDs. For example, when the operation mode includes the waste removal mode and absorption acceleration mode, a first operation mode LED may correspond to the waste removal mode, and a second operation mode LED may correspond to absorption acceleration mode. That is, when the currently selected operation mode is the waste removal mode, light may be irradiated to the outside from the first operation mode LED, and when the currently selected operation mode is absorption accelerating mode, light may be irradiated to the outside from the second operation mode LED.

The battery LED 236 may visually provide the user with information related to a remaining capacity of the battery 237. For example, a color of the battery LED 236 may be changed or a blinking cycle thereof may be changed on the basis of the remaining capacity of the battery 237.

For example, when the remaining capacity of the battery 237 is greater than or equal to a reference capacity, the color of the battery LED 236 may be displayed in a first color (e.g., green) or the battery LED 236 may not blink. Meanwhile, when the remaining capacity of the battery 237 is less than the reference capacity, the battery LED 236 may be displayed in a second color (e.g., red) or the battery LED 236 may blink.

The battery 237 may supply power for the operation of various components included in the main body 2. For example, the battery 237 may supply power required for the operation of the components included in the board 233 and the driving of the various components included in the head part 21.

When the main body 2 is mounted on the cradle 4 or connected to an external power supply through the power supply terminal connection hole 252 of the lower cover 251, the battery 237 may be charged by power supplied from the cradle 4 or the outside.

The speaker modules 241, 242, 243, and 244 may output sounds such as beep, voice, and various sounds according to an operating state of the main body 2.

To this end, the speaker module 241, 242, 243, and 244 may include a speaker 241 outputting the sound, a speaker seating portion 242 fixed to the board 233 and allowing the speaker 241 to be seated thereon, a speaker holder 243 fastened to the speaker seating portion 242 and fixing the speaker 241 seated on the speaker seating portion 242, and a sealing portion 244 provided between the speaker 241 and the speaker holder 243.

For example, the speaker 241 may provide various types of information in a sound form such as power on/off of the main body 2, setting of an operation mode, a battery status, whether the cap assembly 3 is installed, connection to the cradle 4, and the like.

The speaker modules 241, 242, 243, and 244 will be described in more detail with reference to FIG. 4.

Figure 4:
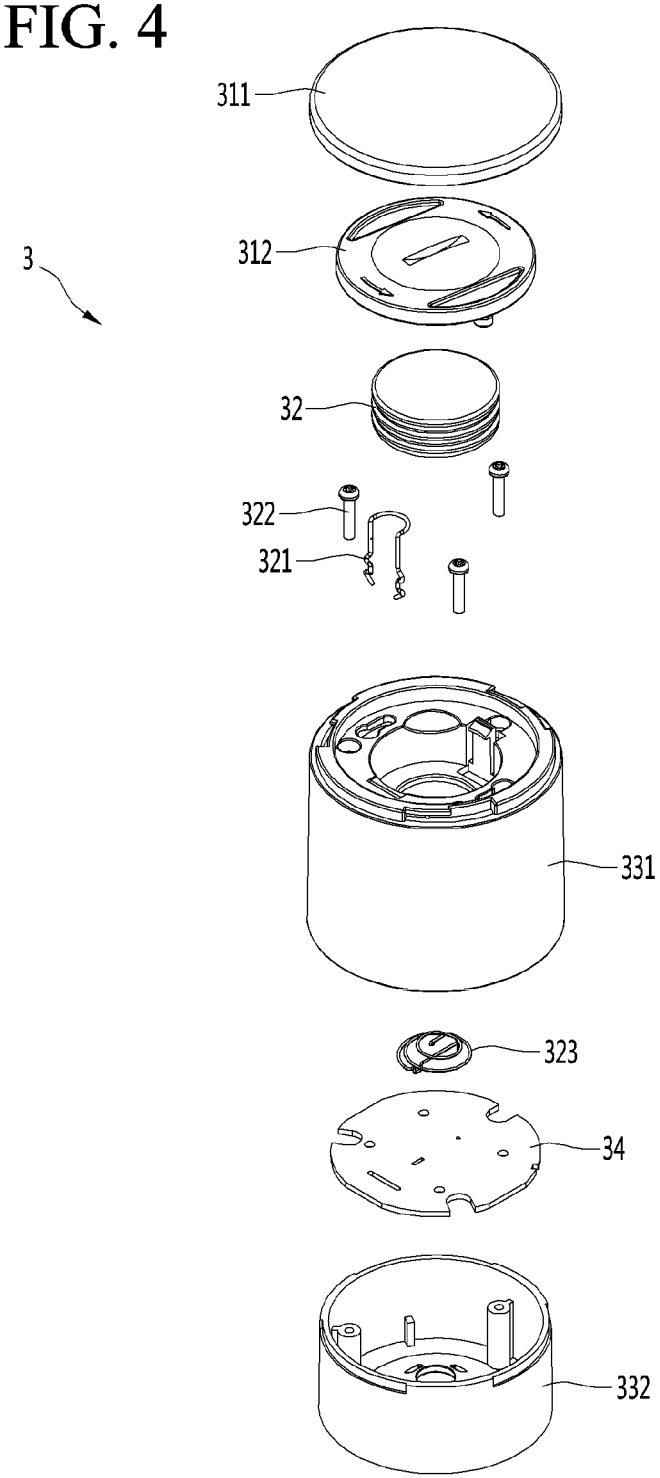
FIG. 4 is a cross-sectional view showing a speaker module included in a main body of a skin care device according to an embodiment.

FIG. 4 is a cross-sectional view of a speaker module included in a main body of a skin care device according to an embodiment.

Referring to FIGS. 3 and 4, a speaker hole 229 may be formed at the case 223 to smoothly transfer a sound output to the speaker 241 to the outside. In addition, the speaker holder 243 may be provided with an opening for smoothly transferring the sound output from the speaker 241 to the outside. An area of the opening may be equal to or larger than that of the speaker hole 229 but is not necessarily limited thereto.

A portion of the speaker 241 is opened to the outside through the opening formed at the speaker holder 243 and the speaker hole 229, and the sound output from the speaker 241 may be transferred to the outside through the speaker hole 229.

Meanwhile, a bottom surface of the speaker seating part 242, that is, a surface in contact with the board 233 may be spaced apart from a seating surface of the speaker 241 by a predetermined distance when the speaker 241 is seated. To this end, the speaker seating portion 242 may be provided with a stopper protruding by a predetermined height from a position off the center of the bottom surface. The speaker 241 may be in contact with the stopper so as to be seated on the speaker seating portion 242.

As the speaker holder 243 is fastened to the speaker seating portion 242, an echo space 245 may be formed by the seating surface of the speaker 241, the bottom surface of the speaker seating portion 242, the stopper, and the speaker holder 243. As the echo space 245 is formed, sound quality of the sound output from the speaker 241 may be further improved.

The skin care device 1 according to an embodiment of the present disclosure may be used to remove wastes from the skin or accelerate absorption of active ingredients and may be frequently in contact with foreign matter such as water or cosmetic products. In this case, there is a possibility that water or foreign matter flows into the main body 2, which may lower performance of the main body 2 or cause fault.

In particular, when water or foreign matter is introduced through the speaker hole 229 of the case 223, sound quality of the sound output from the speaker 241 may be degraded. The speaker 241 may be implemented as a known waterproof speaker to minimize an influence of introduced water or foreign matter, but if water or foreign matter is introduced into the echo space 245 through a gap between the speaker 241 and the speaker holder 243, sound quality of the output sound may be degraded.

In order to prevent water or foreign matter from entering the echo space 245, a sealing portion 244 may be provided between the speaker 241 and the speaker holder 243. The sealing portion 244 may also have an opening for smoothly transferring sound output from the speaker 241 to the outside. An area of the opening may be larger than or equal to the area of the opening formed at the speaker holder 243.

The sealing portion 244 may be implemented as rubber, silicon, or the like. Since a phenomenon in which water or foreign matter is introduced into the echo space 245 is prevented by the sealing portion 244, the sound quality of the sound output from the speaker 241 may be maintained.

FIG. 3 will be described again.

The lower cover 251 may be coupled to the case 223 or the inner frame 231 to cover a lower portion of the main body 2 to protect various components in the case 223.

The lower cover 251 may have a through hole allowing the main body contact terminal 253 and the cradle contact terminal 412 to be in contact with each other therethrough, and a power supply terminal connection hole 252 for connecting an external power supply device to the battery 237 may be formed.

According to an embodiment, a magnetic material 254 for preventing shaking or tilting of the main body 2 when the main body 2 is mounted on the cradle 4 is further provided between the lower cover 251 and the inner frame 231. For example, the magnetic material 254 may prevent shaking or tilting of the main body 2 using a magnetic force with a magnetic material 414 provided at the cradle 4.

Figure 5:
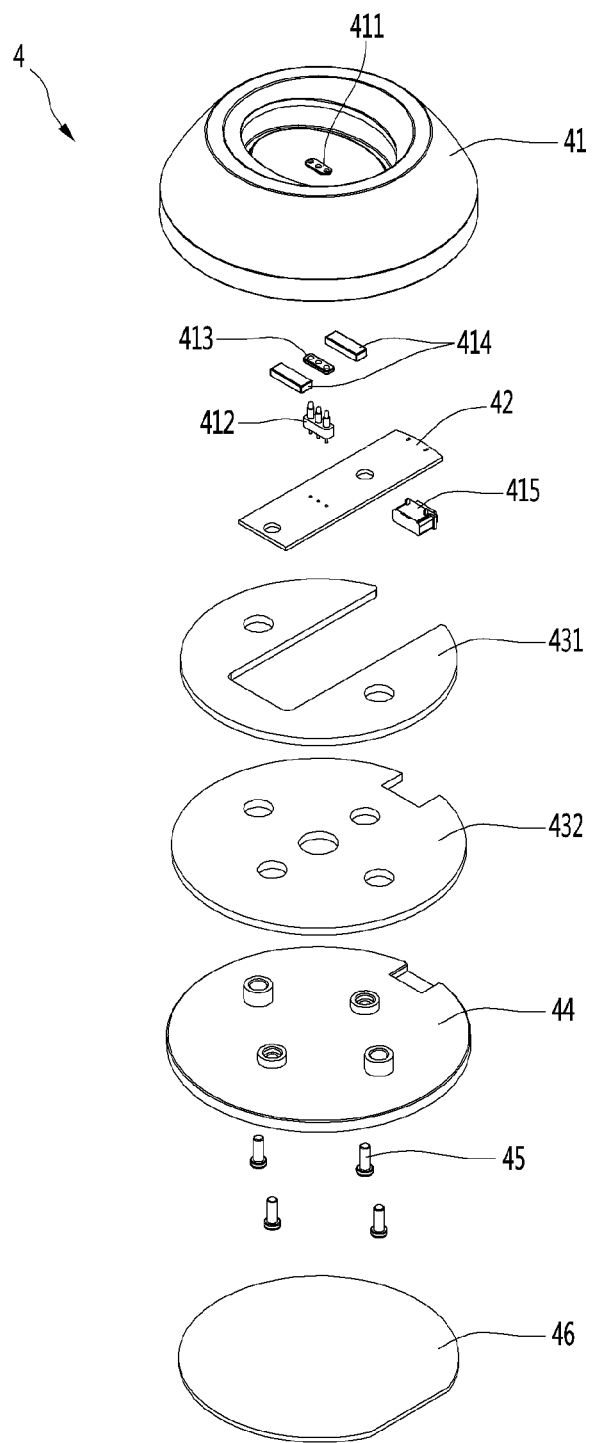
FIG. 5 is an exploded perspective view of a cap assembly included in a skin care device according to an embodiment of the present disclosure.
Figure 6:
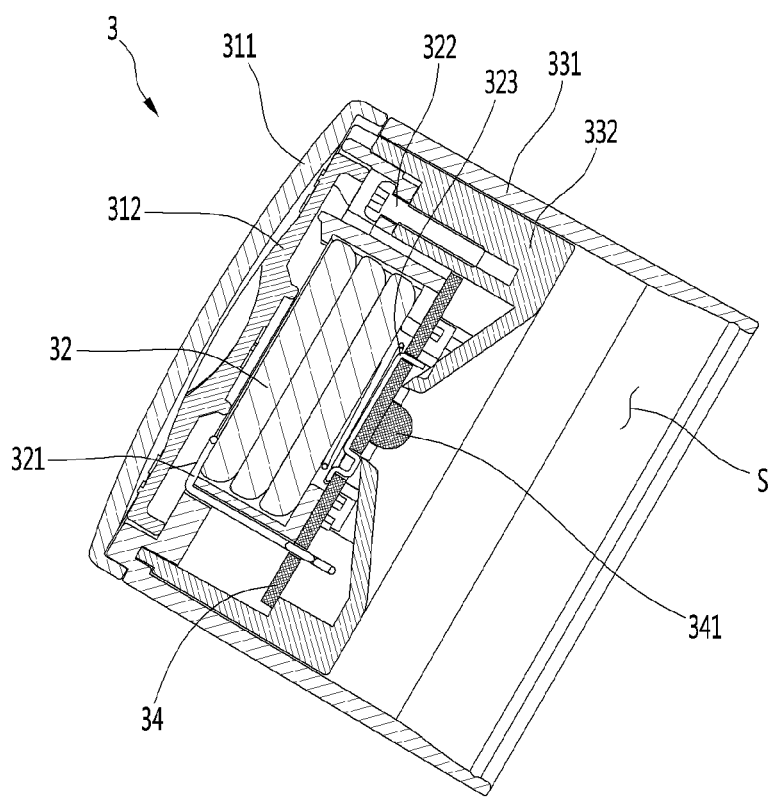
FIG. 6 is a cross-sectional view of a cap assembly included in a skin care device according to an embodiment of the present disclosure.

FIG. 5 is an exploded perspective view of a cap assembly included in a skin care device according to an embodiment of the present disclosure, and FIG. 6 is a cross-sectional view of a cap assembly included in a skin care device according to an embodiment of the present disclosure.

Referring to FIGS. 5 and 6, the cap assembly 3 may include a top cover 311, a battery cover 312, a battery 32, a battery fixing portion 321, a spring terminal 323, an outer body 331, an inner body 332, and a sterilization module 34.

The top cover 311 may be mounted at one end of the outer body 331 to protect various components of the cap assembly 3 from the outside. As shown in FIG. 5, when the outer body 331 is formed in a cylindrical shape, the top cover 311 may have a disk shape. The top cover 311 and the outer body 331 may be formed of hard plastic or metal to protect internal components from an external impact.

The battery cover 312 provided between the top cover 311 and the outer body 331 may cover one surface of the battery 32 accommodated in the outer body 331 and the inner body 332. Accordingly, the battery 32 may be dually protected by the top cover 311 and the battery cover 312.

The battery 32 may supply power for the operation of components (e.g., the sterilization module 34, etc.) included in the cap assembly 3. The battery 32 may be exposed to the outside as the top cover 311 and the battery cover 312 are separated from the outer body 331, and the user may separate the battery 32 from the outer body 331 and the inner body 332.

The battery fixing portion 321 may fix the battery 32 accommodated in the outer body 331 and the inner body 332 to prevent the battery 321 from being separated by the spring terminal 323.

In addition, one end of the battery fixing portion 321 may be connected to one of a positive electrode and a negative electrode of the battery 32 and the other end thereof may be connected to the sterilization module 34. To this end, the battery fixing portion 321 may be implemented as a conductor (e.g., metal, etc.) in which current flows.

In order to fix the battery 32, the battery fixing portion 321 extends from the other end connected to the sterilization module 34 toward the top cover 311, and one end of the battery fixing portion 321 may be formed to be sloped with a portion extending from the other end so as to be in contact with the electrode of the battery 32.

One end of the spring terminal 323 may be connected to an electrode different from the electrode to which the battery fixing portion 321 is connected, among the positive electrode and the negative electrode of the battery 32, and the other end thereof may be connected to the sterilization module 34. That is, as each of the battery fixing portion 321 and the spring terminal 323 is connected to the sterilization module 34, the sterilization module 34 may receive power from the battery. To this end, the spring terminal 323 may also be implemented as a conductor through which current flows.

Meanwhile, the spring terminal 323 may exert an elastic restoring force to push the battery 32 toward the battery cover 312. Accordingly, contact between the battery 32 and the battery fixing portion 321 and between the battery 32 and the spring terminal 323 may be made more effectively.

The outer body 331 may form an appearance of the cap assembly 3 together with the top cover 311. The outer body 331 may form a space for accommodating the battery 32, the inner body 332, and the sterilization module 34 therein and form an accommodation space S for accommodating the contact probe 211 when mounted on the main body 2. In order for the cap assembly 3 to be mounted on the main body 2, an opening may be formed on one surface of the outer body 331 (e.g., the surface opposite to the surface on which the top cover 311 is mounted). In order for the contact probe 211 to be accommodated in the accommodation space S through the opening, an inner diameter of the opening may be larger than an outer diameter of the contact probe 211 or an outer diameter of the contact probe fastening portion 222.

The inner body 332 may be accommodated in the outer body 331 and fastened to the outer body 331. For example, the outer body 331 and the inner body 332 may be fastened to each other by a fastening member such as a screw 322.

A sterilization module 34 may be disposed between the outer body 331 and the inner body 332. In this case, in order to allow ultraviolet light output from the ultraviolet light emitting device 341 provided in the sterilization module 34 to be irradiated to the contact probe 211, the inner body 332 may have an opening exposing the ultraviolet light emitting device 341 to the accommodation space S. An opening may be formed to expose it. According to an embodiment, in order to prevent water or foreign matter from coming into contact with the ultraviolet light emitting device 341, a transparent material or a transparent film allowing ultraviolet light to be transmitted therethrough may be further formed at the opening of the inner body 332.

The sterilization module 34 may perform a sterilization operation to remove bacteria that may occur due to continuous use of the contact probe 211. For example, the sterilization module 34 may correspond to an ultraviolet sterilization module that emits ultraviolet light to the contact probe 211. The sterilization module 34 may include an ultraviolet light emitting device 341 that emits ultraviolet light.

Ultraviolet (UV) light may be classified into UV-A (315-400 nm), UV-B (285-315 nm), and UV-C (200-280 nm) depending on a wavelength. For example, the ultraviolet light emitting device 341 provided at the sterilization module 34 may be implemented as a UV-C LED for irradiating light having the UV-C wavelength.

Since ultraviolet light having the UV-C wavelength cannot be visually checked by the user, it may be difficult for the user to check whether the sterilization module 34 is operating properly. According to an embodiment, the sterilization module 34 may further include an LED (not shown) that emits light of a specific color (e.g., blue). The LED may irradiate light of the specific color when the ultraviolet light emitting device 341 irradiates ultraviolet light. The user may easily check whether the sterilization module 34 is operating by checking the specific color with the naked eyes.

Figure 7:
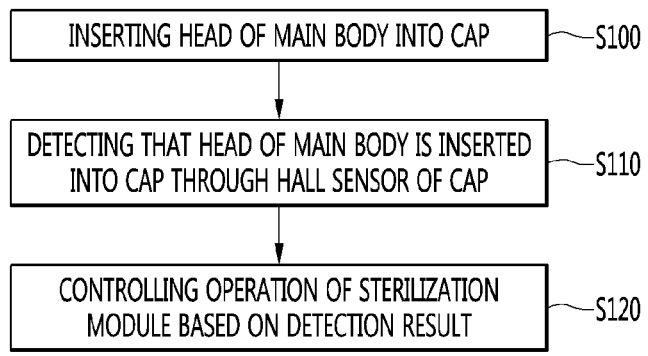
FIG. 7 is a flowchart illustrating a sterilization operation of a cap assembly according to an embodiment of the present disclosure.

FIG. 7 is a flowchart for explaining a sterilization operation of the cap assembly according to an embodiment of the present disclosure.

The sterilization module 34 may operate as the cap assembly 3 is mounted on the main body 2. The sterilization module 34 or the cap assembly 3 may further include a hall sensor (not shown) detecting whether the cap assembly 3 is mounted on the main body 2. In this case, the sterilization module 34 may further include a processor (e.g., a microprocessor) that controls the operation of the ultraviolet light emitting device 341 based on the detection information of the hall sensor.

In this regard, referring to FIG. 7, the head part (or head) 21 of the main body 2 may be inserted into the cap assembly 3 (S100).

For example, after the user uses the main body 2 of the skin care device 1, the user may insert the head part 21 of the main body 2 into the cap assembly 3. Accordingly, the contact probe 211 of the head part 21 may be accommodated in the accommodation space S of the cap assembly 3.

The cap assembly 3 may detect that the head part 21 of the main body 2 is inserted into the cap assembly 3 through the hall sensor (S110).

The hall sensor may detect a change in a magnetic field caused by the magnetic material 214 provided at the head part 21 of the main body 2, thereby detecting that the head part 21 is inserted into the cap assembly 3.

The cap assembly 3 may control the operation of the sterilization module 34 based on the detection result (S120).

When it is detected that the head part 21 is inserted into the cap assembly 3 by the hall sensor, the sterilization module 34 may perform a sterilization operation on the contact probe 211 accommodated in the accommodation space S.

Specifically, the sterilization module 34 may control the ultraviolet light emitting device 341 to irradiate ultraviolet light to perform sterilization operation on the contact probe 211 accommodated in the accommodation space S of the cap assembly 3. For example, the sterilization operation may be performed for about 40 seconds to 1 minute but is not necessarily limited thereto. According to an embodiment, the controller of the main body 2 may output a voice indicating that the sterilization operation is performed through the speaker 241.

Although not shown, the sterilization module 34 may change a sterilization operation time, strength, and the like based on the degree of rotation of the cap assembly 3 relative to the main body 2. For example, when the user mounts the cap assembly 3 on the main body 2 and then rotates the cap assembly 3 in a predetermined direction, the sterilization module 34 may set a time of a sterilization operation according to a rotation angle of the cap assembly 3 or adjust strength of light irradiated from the ultraviolet light emitting device 341.

In FIGS. 6 and 7, a hall sensor is included in the cap assembly 3 and it is detected that the cap assembly 3 is mounted on the main body 2 through the hall sensor (or the head part 21 of the main body 2 is inserted into the cap assembly 3). However, in some embodiments, a proximity sensor, instead of the hall sensor, may be provided at the cap assembly 3. For example, the proximity sensor may be disposed at the sterilization module 34 so as to face the accommodation space S and detect whether the contact probe 211 is in proximity. When the contact probe 211 is accommodated in the accommodation space S, the proximity sensor may detect that the cap assembly 3 is mounted on the main body 2.

Figure 8:
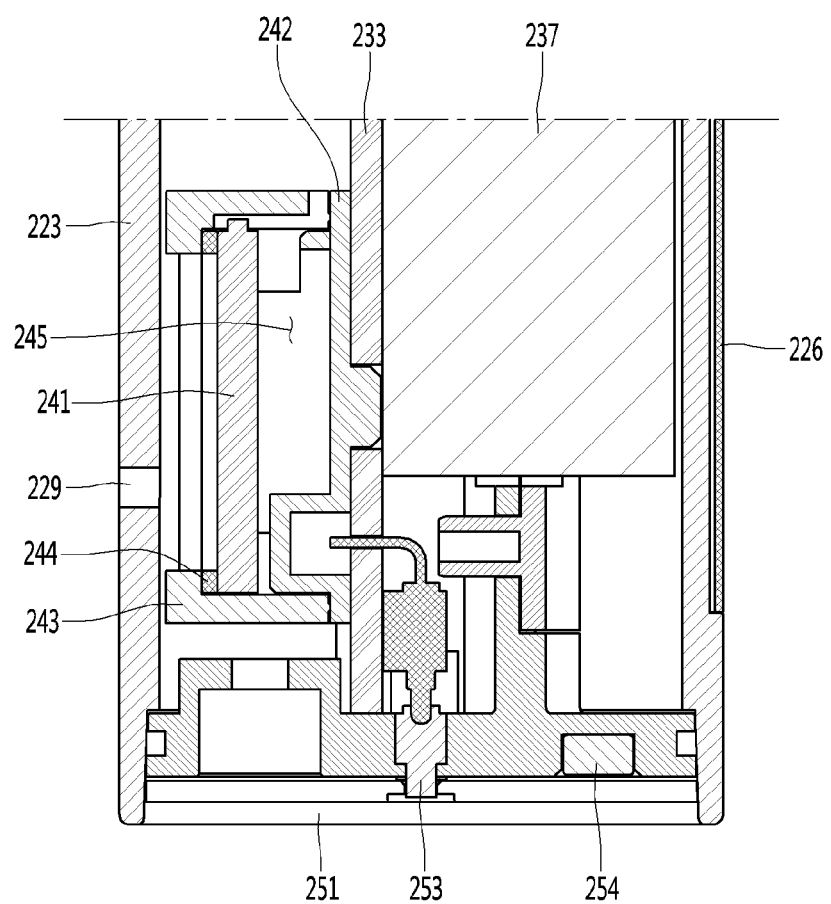
FIG. 8 is an exploded perspective view of a cradle included in a skin care device according to an embodiment of the present disclosure.
Figure 9:
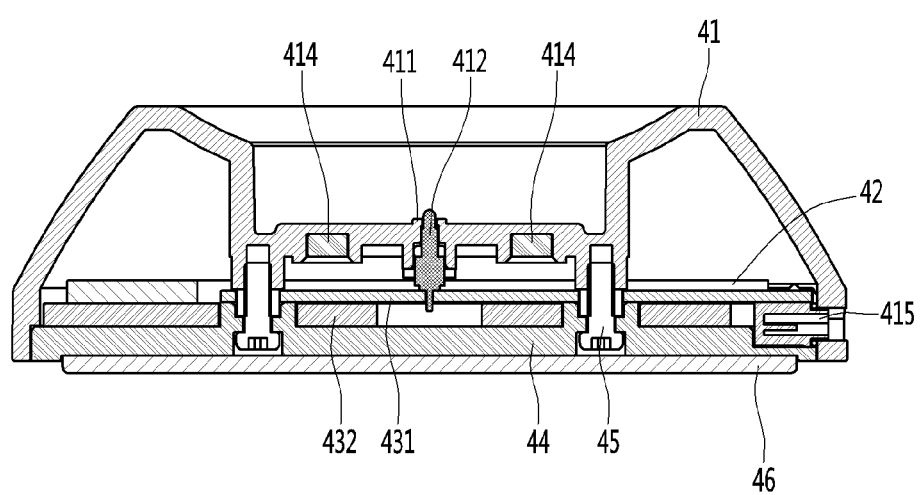
FIG. 9 is a cross-sectional view of the cradle according to an embodiment of the present disclosure.

FIG. 8 is an exploded perspective view of a cradle included in a skin care device according to an embodiment of the present disclosure and FIG. 9 is a cross-sectional view of a cradle according to an embodiment of the present disclosure.

Referring to FIGS. 8 and 9, the cradle 4 includes an upper case 41 and a lower cover 44, and an accommodation space in which the charging module 42 and at least one support plate 431 and 432 are accommodated may be formed between the upper case 41 and the lower cover 44. The upper case 41 and the lower cover 44 may be fastened to each other through a fastening member such as a screw 45.

The upper case 41 may form an overall appearance of the cradle 4. The upper case 41 may have an accommodation space for accommodating a part of the main body 2. As described above with reference to FIGS. 1 and 2, the upper case 41 has a cylindrical shape that becomes wider toward the lower side, thereby stably supporting the main body 2 when the main body 2 is mounted. In addition, a minimum inner circumference of the upper case 41 is formed to be larger than an outer circumference of the lower portion of the case 223, so that the lower portion of the case 223 may be accommodated in the upper case when the main body 2 is mounted on the cradle 4.

According to an embodiment, the cradle 4 may further include a magnetic material 414 which interacts with the magnetic material 254 provided at the lower portion of the main body 2 when the main body 2 is mounted on the cradle 4, thereby effectively fixing and supporting the main body 2 to the cradle 4. For example, the polarity of the magnetic material 254 provided at the main body 2 and the polarity of the magnetic material 414 provided at the cradle 4 are configured to be different from each other, so that the main body may be effectively fixed to the cradle 4 using attractive force between the magnetic materials 254 and 414.

The charging module 42 may perform an operation of supplying power to the battery 237 of the main body 2 when the main body 2 is mounted on the cradle 4. Specifically, a contact terminal connection hole 411 may be formed on one surface of the upper case 41, and a portion of the cradle contact terminal 412 connected to the charging module 42 may be exposed to the outside through the contact terminal connection hole 411. According to an embodiment, a sealing portion 413 for preventing an introduction of water or foreign matter into the upper case 41 may be provided between the contact terminal connection hole 411 and the cradle contact terminal 412.

When the main body 2 is mounted on the cradle 4, a portion of the externally exposed cradle contact terminal 412 may be in contact with the main body contact terminal 253 in the main body 2 through a through hole formed at the lower cover 251 of the main body 2. As the cradle contact terminal 412 and the main body contact terminal 253 are in contact with each other, the charging module 42 may supply power supplied from the outside to the battery 237. To this end, the charging module 42 may have a power supply terminal 415 and supply power supplied from an external power supply connected through the power supply terminal 415 to the battery 237 through the cradle contact terminal 412 and the main body contact terminal 253.

According to an embodiment, the charging module 42 may obtain information about a charging state of the battery 237 and stop supplying power to the battery 237 when the battery 237 is fully charged.

The at least one support plate 431 and 432 provided between the upper case 41 and the lower cover 44 may increase the weight of the cradle 4, thereby preventing a phenomenon that the cradle 4 and the main body 2 falls in one direction when the main body 2 is shaken or tilted, thus stably supporting the main body 2. To this end, the support plates 431 and 432 may be implemented with a metal having a predetermined weight or the like.

As shown in FIG. 8, it is assumed that the support plates 431 and 432 include a first support plate 431 and a second support plate 432 disposed under the first support plate 431. In this case, an accommodation recess for accommodating the charging module 42 may be formed at the first support plate 431. The charging module 42 may be accommodated in the accommodation recess and seated on an upper surface of the second support plate 432. Accordingly, since a height from the second support plate 432 to the charging module 42 is minimized, the volume (or height) of the cradle 4 may be reduced.

The lower cover 44 may be fastened to the upper case 41 to accommodate the charging module 42 and the support plates 431 and 432 in the cradle 4. The upper case 41 and the lower cover 44 may be fastened to each other through a fastening member such as a screw 45. Here, in order to effectively fix the charging module 42 and the support plates 431 and 432 accommodated between the upper case 41 and the lower cover 44, the screw 45 may be fastened from the lower cover 44 to the upper case 41 through the charging module 42 and the support plates 431 and 432. The charging module 42 and the support plates 431 and 432 may include at least one through hole through which the screw 45 passes.

According to an embodiment, a pad 46 for suppressing a horizontal movement such as sliding or the like of the cradle 4 may be provided on a bottom surface of the lower cover 44. The pad 46 may be attached to the bottom surface of the lower cover 44. The pad 46 may be formed of a material such as silicon or rubber.

Figure 10:
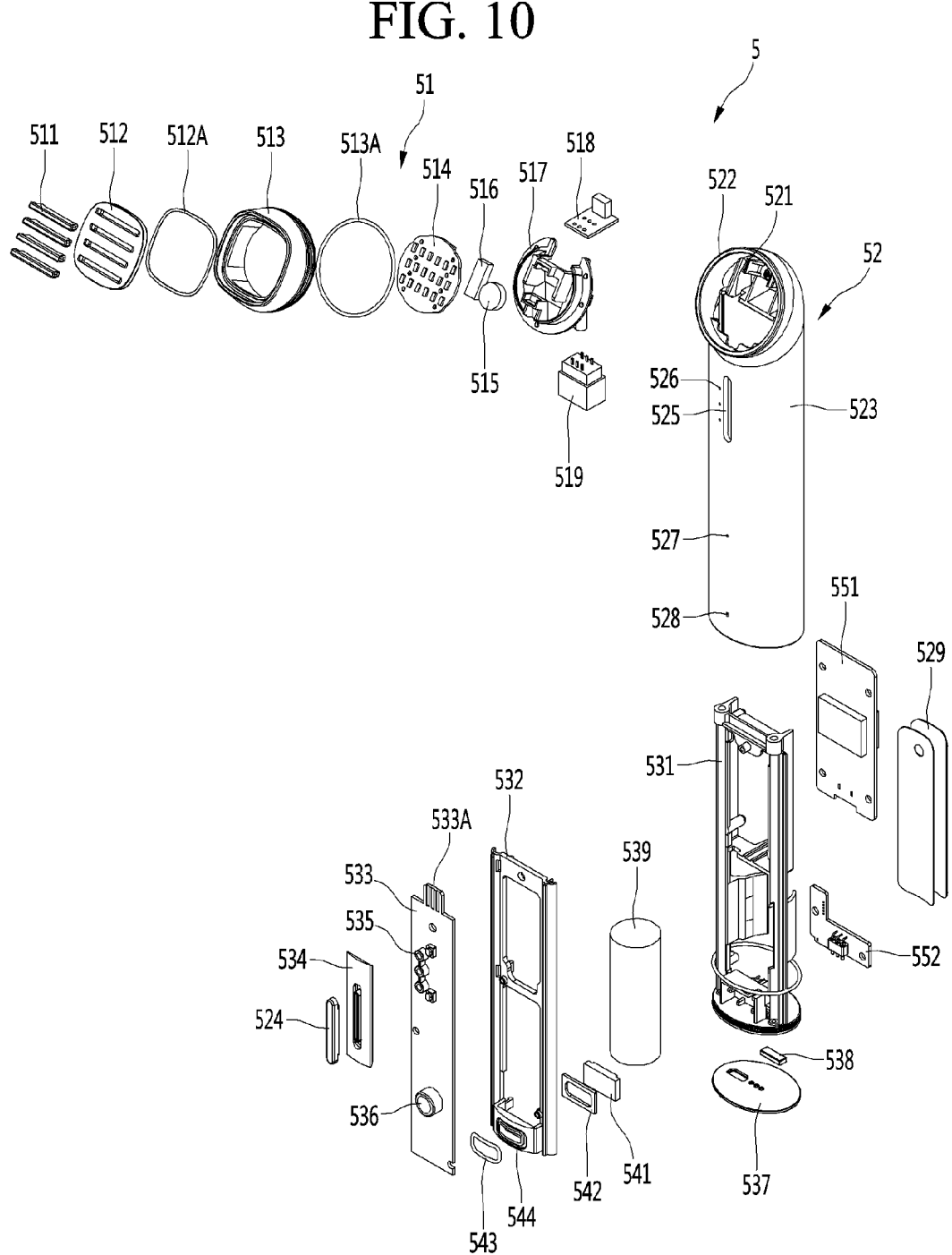
FIG. 10 is an exploded perspective view of a main body included in a skin care device according to another embodiment of the present disclosure.

FIG. 10 is an exploded perspective view of a main body included in a skin care device according to another embodiment of the present disclosure.

The skin care device according to an embodiment shown in FIG. 10 may correspond to a device which improves elasticity of the skin by applying a high frequency stimulation, electrical muscle stimulation (EMS), and the like to the skin or accelerates activation of collagen or elastin contained in the skin and activation of cells by irradiating the skin with light of a specific color.

The skin care device shown in FIG. 10 also includes a cap assembly 3 and a cradle 4 similarly to the skin care device shown in FIGS. 1 to 2 but may include a main body 5 in which some component are changed with respect to the main body 2 shown in FIGS. 1 and 2. Some configurations may include the main body 5 to be modified. Therefore, hereinafter, those among the components included in the main body 5 which are different from those of the main body 2 described above in FIG. 3 will be described with reference to FIG. 3.

Referring to FIG. 10, the main body 5 may include a head part 51 and a body part 52.

The head part 51 stimulates a skin part of the user in various ways, thereby improving elasticity of the skin or accelerates activation of collagen, elastin, or skin cells of the skin to improve wrinkles or improve skin regeneration.

The head part 51 may include a contact probe 511, a head part cover 512, a head part body 513, an LED module 514, a vibration motor 515, a holder 517, a head part control module 518, and head part socket 519.

The contact probe 511 may directly contact the skin of the user to transmit a high frequency stimulation or a low frequency stimulation to the skin of the user. The contact probe 511 may be implemented with a plurality of contact probes, and each of the plurality of contact probes may form an electrode of a positive electrode or a negative electrode. For example, when the contact probe 511 includes four contact probes as shown in FIG. 10, each of the polarities of the contact probes may be formed so that the positive electrode and the negative electrode cross each other. In order to form an electrode on the contact probe 511, the contact probe 511 may be formed of a conductive material such as metal.

The contact probe 511 may transfer the high frequency stimulation to the skin as high frequency power is applied under the control of an electrical stimulation control module 551 to be described later or transfer the low frequency stimulation to the skin by applying a microcurrent.

For example, the high frequency power may have a voltage of about 100V and a frequency of about 1 Mhz. As the high frequency power is applied, heat may be applied to a dermal layer in the skin by the high frequency stimulation transferred to the skin. As heat is applied to the dermal layer, substances that improve elasticity of the skin may be more actively generated.

Meanwhile, in the case of delivering the low frequency stimulation to the skin, the microcurrent may correspond to about 1000 mA but is not necessarily limited thereto. When such microcurrent is applied, adjacent muscles in the skin may be forcibly moved and elasticity of the skin may be restored by movement of the adjacent muscles in the skin.

The head part cover 512 may form an opening for protruding at least a portion of the contact probe 511 to the outside. The head part cover 512 may be fastened to one surface of the head part body 513, thereby protecting components in the head part body 513 from the outside. In some embodiments, a head cover sealing member 512A may be provided between the head part cover 512 and the head part body 513. The head cover sealing member 512A may prevent water or other foreign matter from penetrating into the head part 51 through a gap between the head part cover 512 and the head part body 513. For example, the head cover sealing member 512A may have a ring shape such as a rectangle or a circle and may be formed of a material such as rubber or silicon.

In particular, the head part cover 512 may be implemented with a transparent material (acrylic, plastic, etc.) in order to irradiate light emitted from the LED module 514 accommodated in the head part 51 to the skin of the user.

The head part body 513 may form an appearance of the head part 51. The head part body 513 may be fastened to the head part body fastening portion 522 and the head part cover 512 of the body part 52 to form an accommodation space for accommodating various components of the head part 51 therein.

In addition, as the head part body 513 is fastened to the head part body fastening portion 522, the contact probe 511 fastened to the head part body 513 and the head part cover 512 may be fixed to the body part 52.

According to an embodiment, a head part body sealing member 513A may be provided between the head part body 513 and the head part body fastening portion 522. The head part body sealing member 513A may prevent water or other foreign matter from penetrating into the head part 51 through a gap between the head part body 513 and the head part body fastening portion 522. Similar to the head cover sealing member 512A, the head part body sealing member 513A may have a circular ring shape and may be formed of a material such as rubber or silicon.

The LED module 514 may include at least one LED for irradiating light onto the surface of the skin of the user to increase a temperature of the skin surface of the user. The at least one LED included in the LED module 514 may include a red LED emitting infrared light or red light having about 630 nm wavelength. For example, the LED module 514 may irradiate light to the skin surface when the contact probe 511 applies high frequency stimulation to the skin.

Light emitted from the LED module 514 may be irradiated to the skin surface through the head part cover 512. As the light is irradiated onto the skin surface, the temperature of the skin surface may increase. That is, the temperature of the skin may be increased by the high frequency stimulation and the light, and as a result, production of an elastic substance in the skin may be accelerated.

The vibration motor 515 may transfer vibration to the skin by vibrating the contact probe 511 or the head part cover 512. As the contact probe 511 or the head part cover 512 vibrates, the skin vibrates directly, thereby accelerating activation of skin cells and improving skin elasticity.

Various components provided in the head part 51 may be mounted on or fixed to the holder 517 so as to fix the various components to the main body 5. For example, the holder 517 may be provided with a mounting space or accommodation space in which the LED module 514, the vibration motor 215, the head part control module 518, and the head part socket 519 are mounted or accommodated.

The holder 517 may be fastened to the holder fastening portion 521 of the body part 52 to be described later so as to be fixed to the body part 52.

The head part control module 518 may control an operation of the components included in the head part 51. For example, the head part control module 518 may control an operation of the LED module 514 and/or vibration motor 515. The head part control module 518 may include a controller such as an integrated circuit or a microcomputer and the controller may control the operation of the components included in the head part 51.

According to an embodiment, the head part 51 may further include a magnetic material 516 for detecting whether the head part 51 or the contact probe 511 is accommodated in the cap assembly 3. When the contact probe 511 is accommodated in the accommodation space of the cap assembly 3 as the cap assembly 3 is mounted on the head part 51 of the main body 5, a hall sensor (not shown) provided at the cap assembly 3 may detect a change in a magnetic field due to the proximity of the magnetic material 516 to detect that the contact probe 511 is accommodated.

Referring to FIG. 10, the body part 52 may include a holder fastening portion 521, a head part body fastening portion 522, a case 523, a button portion 524, and an electrode plate 529. In addition, the body part 52 may include an inner frame 531, an inner frame cover 532, a board 533 including a main control module, an operation mode LED 535, a battery LED 536, a lower cover 537, speaker modules 541, 542, 543, and 544, and an electrical stimulation control module 551 inside and at a lower portion thereof.

The holder fastening portion 521 may be fastened to the holder 517 through a screw. The holder 517 may be fastened to the holder fastening portion 521 so as to be fixed to the body part 52.

The head part body fastening portion 522 may be fastened to the head part body 513, thereby fixing the contact probe 511 and the head part cover 512 to the body part 52. As described above, various components of the head part 51 may be accommodated in the space formed by the head part cover 511, the head part main body 513, and the body part 52.

The case 523 may have a button portion through recess 525 allowing the button portion 524 connected to the internal board 533 or the button fixing portion 534 to protrude to the outside. In addition, the case 523 may further include light irradiation holes 526 and 527 for irradiating light emitted from each of the operation mode LED 535 and the battery LED 536 connected to the internal board 533 to the outside.

Various components inside the main body 5 may be mounted on or connected to the inner frame 531. For example, the holder fastening portion 521, the board 533, the battery 539, the lower cover 537, and the electrical stimulation control module 551 may be connected to or mounted on the inner frame 531.

The board 533 may be provided with a controller for controlling an overall operation of the main body 5. The controller may control strength of a voltage or current applied to the contact probe 511, the operation of the LED module 514, the operation of the vibration motor 515, and the like according to the operation mode of the main body 5.

In more detail, when power of the main body 5 is turned on and the operation mode of the main body 5 is selected, the controller provided at the board 533 may directly control the operation of the components included in the head part 51 according to the selected operation mode or may indirectly control the operation of the components by transmitting a control signal to the head part control module 518 according to the operation mode.

In the following description, it is assumed that the controller directly controls the operation of the components included in the head part 51.

For example, when the operation mode is selected as the high frequency stimulation mode, the controller may control the electrical stimulation control module 551 to apply high frequency power to the contact probe 511. In this case, the contact probe 511 may transmit high frequency stimulation to the skin of the user. In addition, the controller may control the LED module 514 to irradiate light onto the skin of the user. Due to the high frequency stimulation and light irradiation, a skin temperature of the user may be increased to accelerate production of an elastic material of the skin. Meanwhile, the controller may control driving of the vibration motor 515 to vibrate the skin of the user.

Meanwhile, when the operation mode is selected as the low frequency stimulation mode, the controller may control the electrical stimulation control module 551 to apply a microcurrent to the skin of the user through the contact probe 511. In addition, the controller may directly vibrate the skin by driving the vibration motor 515. The skin is moved by the application of the microcurrent and vibration of the skin, thereby restoring elasticity of the skin or improving wrinkles.

The board 533 may include a button portion 524 for turning on/off power of the main body 5 or changing the operation mode of the main body 2, at least one operation mode LED 535 indicating information on the currently selected operation mode, and a battery LED 536 indicating a battery status.

Here, the operation mode LED 535 may inform the user of information on the currently selected operation mode. To this end, the operation mode LED 535 may include a plurality of operation mode LEDs. For example, when the operation mode includes a high frequency stimulation mode and a low frequency stimulation mode, a first operation mode LED may correspond to the high frequency stimulation mode, and a second operation mode LED may correspond to the low frequency stimulation mode. That is, when the currently selected operation mode is the high frequency stimulation mode, light is irradiated to the outside from the first operation mode LED, and when the currently selected operation mode is the low frequency stimulation mode, light may be irradiated to the outside from the second operation mode LED.

The speaker modules 541, 542, 543, and 544 may output sounds such as beep, voice, and various sounds depending on an operating state of the main body 5.

To this end, the speaker modules 541, 542, 543, and 544 may include a speaker 241 for outputting the sound and a speaker holder 542 fastened to the inner frame 531 and fixing the speaker 541. In addition, the speaker module may include a speaker accommodating portion 544 provided in the inner frame cover 532 and forming a space for accommodating the speaker 541 and the speaker holder 542 as the inner frame 531 and the inner frame cover 532 are fastened, and a sealing portion 543 provided between the speaker accommodating portion 543 and the case 523.

In the embodiment illustrated in FIG. 10, an echo space may be provided between the speaker 541 and the inner frame 531. To this end, the inner frame 531 may include an echo space forming portion in contact with the speaker 541 and forming an echo space with the speaker 541.

In order to transfer the sound output from the speaker 541 to the outside, the speaker holder 542, the sealing portion 543, and the speaker accommodating portion 544 may include an opening, and the case 523 may include a speaker hole 528. Here, the sealing portion 543 may be disposed between the case 523 and the speaker accommodating portion 544 or disposed between the speaker 541 and the speaker holder 542 to prevent water or foreign matter injected through the speaker hole 528 from penetrating into the echo space.

The electrical stimulation control module 551 may apply high frequency stimulation to the skin by applying a high frequency power to the contact probe 511 under the control of the controller provided in the board 533 or apply microcurrent to the skin by applying power having a low magnitude. To this end, the contact probe 511 and the electrical stimulation control module 551 may be electrically connected to each other.

According to an embodiment of the present disclosure, the skin care device includes the contact probe in which a positive electrode or negative electrode is formed according to an operation mode, an ultrasonic resonator, a vibration motor, and the like, thereby integrally providing various functions for effective skin case such as removing waste from the skin and accelerating absorption of active ingredients, and the like.

Furthermore, since the sterilization module is disposed at the cap assembly that accommodates the head part provided with the contact probe, it is possible to remove various bacteria that may occur in the contact probe according to the continuous use of the skin care device to maintain cleanliness of the product. In addition, side effects such as skin problems due to bacteria generated in the contact probe may be prevented in advance.

Furthermore, the cap assembly may efficiently operate the sterilization module by automatically detecting accommodation of the head part and also improve user convenience.

Furthermore, a circumference of the contact probe fastened to the fastening portion of the body part in contact with skin is smaller than a circumference of the fastening portion, so that the contact probe may be effectively brought into contact with a local part of the skin.

Furthermore, the speaker module of the body part is implemented to form an echo space to improve sound quality of the speaker and includes the speaker sealing member for shielding the echo space to prevent deterioration of sound quality due to introduction of water or foreign matters.

Furthermore, the cradle mounted at the body part to supply power for charging the battery is formed such that a width of an upper portion of the case forming the appearance is narrower than a width of a lower portion thereof, thus stably supporting the main body.

Although a few embodiments have been shown and described, it will be appreciated by those skilled in the art that changes may be made in these embodiments without departing from the principles and spirit of the invention, the range of which is defined in the appended claims and their equivalents.

Accordingly, the embodiments of the present invention are provided to explain the technical spirit of the present invention but not to limit such spirit, and the scope of the technical spirit of the present invention is not limited by the embodiments of the present invention.

The scope of protection of the present invention should be interpreted by the claims below, and all technical spirits which are in the same scope would be interpreted as being included in the scope of right of the present invention.

What is claimed is:

1. A skin care device comprising:
   a head part brought into contact with skin of a user;
   a battery configured to supply power for operation of the head part;
   a body part having a fastening portion provided at one end to which the head part is fastened and provided with the battery therein; and
   a cap assembly detachably attached to one end of the body part and forming an accommodation space accommodating the head part,
   wherein the cap assembly comprises an ultraviolet light emitting device disposed to irradiate ultraviolet light toward the head part when the cap assembly accommodates the head part.

2. The skin care device of claim 1, wherein
   the head part comprises a magnetic material.

3. The skin care device of claim 1, wherein
   the ultraviolet light emitting device comprises an ultraviolet (UV)-C light emitting diode (LED) configured to irradiate ultraviolet light having a UV-C wavelength.

4. The skin care device of claim 1, wherein
   the cap assembly comprises an outer body forming an appearance of the cap assembly and forming the accommodation space of the head part therein and an inner body accommodated in the outer body, the ultraviolet light emitting device is disposed between the outer body and the inner body, and the inner body has an opening exposing the ultraviolet light emitting device to the accommodation space.

5. The skin care device of claim 4, wherein the cap assembly further comprises a top cover mounted at one end of the outer body, and a battery accommodation space accommodating a battery is provided between the top cover and the outer body.

6. The skin care device of claim 1, further comprising:

a head part sealing member formed between the head part and the fastening portion.

7. The skin care device of claim 1, wherein the head part comprises:

a contact probe brought into contact with the skin of the user and configured to allow a positive electrode or a negative electrode to be formed on a surface thereof according to an operation mode of the skin care device;

an ultrasonic resonator configured to transfer ultrasonic vibration into the skin of the user; and a vibration motor configured to vibrate the contact probe and transfer vibration to the skin.

8. The skin care device of claim 7, wherein the contact probe is fastened to the fastening portion to form a space accommodating the ultrasonic resonator and the vibration motor therein, and a circumference of the surface of the contact probe is smaller than a circumference of the fastening portion.

9. The skin care device of claim 1, wherein the body part comprises:

a case forming an appearance of the body part;

a board provided in the case; and a speaker module disposed between the case and the board.

10. The skin care device of claim 9, wherein the speaker module comprises:

a speaker configured to output sound based on an operation state of the skin care device;

a speaker seating portion fixed to the board and allowing the speaker to be seated thereon; and a speaker holder fastened to the speaker seating portion and configured to fix the speaker, wherein an echo space is provided between the speaker and the speaker seating portion.

11. The skin care device of claim 10, wherein the speaker module further comprises a sealing portion provided between the speaker and the speaker holder to shield the echo space from the outside.

12. The skin care device of claim 1, further comprising:

a cradle mounted at the other end of the body part and configured to supply power for charging the battery.

13. The skin care device of claim 12, wherein the cradle comprises:

a case forming an appearance of the cradle and forming an accommodation space accommodating a portion of the other end of the body part; and a charging module provided in the case and comprising a power supply terminal connected to an external power supply, wherein a width of a lower portion of the case is larger than a width of an upper portion of the case.

14. The skin care device of claim 12, wherein the body part comprises a body part magnetic material disposed to be adjacent to the other end in the case, and the cradle comprises a cradle magnetic material having a polarity different from a polarity of the body part magnetic material.

* * * * *